United States Patent
Yen et al.

(10) Patent No.: US 11,541,551 B2
(45) Date of Patent: Jan. 3, 2023

(54) ROBOTIC ARM

(71) Applicant: National Taiwan University, Taipei (TW)

(72) Inventors: Jia-Yush Yen, Taipei (TW); You-Ting Liao, Taipei (TW); Ching-Yuan Chen, Taipei (TW); Yen-Han Wang, Taipei (TW); Yung-Yaw Chen, Taipei (TW); Ming-Chih Ho, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 745 days.

(21) Appl. No.: 16/528,250

(22) Filed: Jul. 31, 2019

(65) Prior Publication Data
US 2020/0039085 A1 Feb. 6, 2020

(30) Foreign Application Priority Data
Jul. 31, 2018 (TW) ................... 107126565

(51) Int. Cl.
| | |
|---|---|
| *B25J 13/08* | (2006.01) |
| *B25J 9/02* | (2006.01) |
| *B25J 9/16* | (2006.01) |
| *A61B 34/30* | (2016.01) |
| *B25J 18/00* | (2006.01) |

(Continued)

(52) U.S. Cl.
CPC ............. *B25J 13/085* (2013.01); *B25J 9/023* (2013.01); *B25J 9/1666* (2013.01); *B25J 17/025* (2013.01); *B25J 18/007* (2013.01); *G01L 5/226* (2013.01); *A61B 34/30* (2016.02); *A61B 2034/301* (2016.02)

(58) Field of Classification Search
CPC ........ B25J 13/085; B25J 9/023; B25J 9/1666; B25J 17/025; B25J 18/007; B25J 9/1676; G01L 5/226; A61B 34/30; A61B 2034/301; A61B 2034/2065; A61B 2090/061; A61B 2090/064; A61B 2090/066; G05B 2219/40202
USPC ................................... 700/245–264
See application file for complete search history.

(56) References Cited

U.S. PATENT DOCUMENTS 5,294,873 A * 3/1994 Seraji ................. B25J 9/1638
                                            318/568.1
5,907,664 A * 5/1999 Wang ................. A61B 34/70
                                              600/101

(Continued)

FOREIGN PATENT DOCUMENTS

| CN | 104334110 | 2/2015 |
|---|---|---|
| CN | 104519823 | 4/2015 |

*Primary Examiner* — Jaime Figueroa
(74) *Attorney, Agent, or Firm* — Muncy, Geissler, Olds & Lowe, P.C.

(57) ABSTRACT

A robotic arm comprising an operation end, a base, a sensor unit and a control unit is provided. The operation end is connected to the base, and the operation end is configured to reach an operational area. The sensor unit provides a sensor signal according to the force applied by or the motion of an operator. When the operation end reaches the operational area, the control unit sets a fixed position on the robotic arm between the base and the operation end. When the sensor signal from the operator fulfills a default condition, the control unit moves the robotic arm away from the operator, without moving the fixed position on the robotic arm.

9 Claims, 4 Drawing Sheets

(51) Int. Cl.
    *B25J 17/02*     (2006.01)
    *G01L 5/22*      (2006.01)

(56)         References Cited

U.S. PATENT DOCUMENTS

| | | | | |
|---|---|---|---|---|
| 6,659,939 | B2 * | 12/2003 | Moll | A61B 34/30 |
| | | | | 600/102 |
| 6,858,003 | B2 * | 2/2005 | Evans | A61B 34/32 |
| | | | | 606/1 |
| 7,785,320 | B2 * | 8/2010 | Wang | A61B 34/75 |
| | | | | 606/1 |
| 8,004,229 | B2 * | 8/2011 | Nowlin | B25J 3/00 |
| | | | | 318/568.2 |
| 8,167,872 | B2 * | 5/2012 | Schena | A61B 34/37 |
| | | | | 606/1 |
| 9,492,235 | B2 | 11/2016 | Hourtash | |
| 9,757,203 | B2 * | 9/2017 | Hourtash | B25J 9/1607 |
| 9,782,229 | B2 * | 10/2017 | Crawford | A61B 34/30 |
| 10,194,997 | B2 * | 2/2019 | Hourtash | B25J 9/1607 |
| 10,413,370 | B2 * | 9/2019 | Yates | B25J 15/0213 |
| 10,470,830 | B2 * | 11/2019 | Hill | A61B 1/00149 |
| 10,485,617 | B2 * | 11/2019 | Crawford | A61B 34/76 |
| 2007/0173975 | A1 * | 7/2007 | Schena | A61B 34/70 |
| | | | | 700/245 |
| 2008/0221731 | A1 * | 9/2008 | Wang | A61B 17/11 |
| | | | | 901/14 |
| 2011/0264112 | A1 * | 10/2011 | Nowlin | A61B 34/37 |
| | | | | 606/130 |
| 2012/0065470 | A1 * | 3/2012 | Olds | A61B 34/30 |
| | | | | 901/41 |
| 2013/0345718 | A1 * | 12/2013 | Crawford | A61B 90/14 |
| | | | | 606/130 |
| 2015/0202015 | A1 | 7/2015 | Elhawary | |
| 2017/0258533 | A1 * | 9/2017 | Crawford | A61B 34/20 |
| 2019/0175287 | A1 * | 6/2019 | Hill | A61B 34/30 |
| 2020/0054401 | A1 * | 2/2020 | Yu | B25J 9/1633 |

* cited by examiner

ROBOTIC ARM

BACKGROUND

Technical Field

The present invention generally relates to a robotic arm, and more particularly, to a robotic arm for assisting operator.

Related Art

With the advancement of technologies, medical technologies always put safety first while developing new applications. Among these applications, minimally invasive surgeries is one of the major fields of medical technology applications. Surgeons perform minimally invasive surgery via endoscopes and various visualization technologies to prevent causing huge wounds on patient. Hence, compared to conventional surgeries, minimally invasive surgeries have higher wound recovery rate. A patient only needs to have a few small incisions instead of a long one during the surgery, which further minimizes the scar after recovery.

However, such visualization device (e.g. an endoscope) still requires an additional person or object to fix or support during the surgery. For example, it is inevitable that a surgeon is disturbed by the person who operates the endoscope adjacent to the surgeon. On the other hand, since the surgery procedure often takes three to five hours, the stability and accuracy of the endoscope and the cooperation between the endoscope operator and the surgeon might be affected by the fatigue of the endoscope operator. When the endoscope is supported by an object (e.g. a robotic arm or fixture), although the endoscope can be firmly fixed by the object, the degree of coherence between the endoscope and the surgeon will decrease correspondingly. The volume occupied by the robotic arm will also obstruct and affect the overall surgical process Thus, providing a robotic arm to assist surgeons in minimally invasive surgeries is still one of the problems to be solved of contemporary medical technology.

SUMMARY

The robotic arm of the present invention assists an operator based on the location or action of the operator.

The robotic arm of the present invention comprises an operation end, a base, a sensor unit and a control unit. The operation end connected to the base is configured to reach an operation area. The sensor unit provides a sensor signal based on the movement of the operator or the force applied by the operator. When the operation end reaches the operation area, the control unit fix the robotic arm at a position between the base and the operation end. When the sensor signal fulfills a default condition, the control unit moves the robotic arm without interfering with the operator and without moving the fixed position on the robotic arm.

In an embodiment, the robotic arm further comprises a plurality of rotatable joints connected between the operation end and the base. The fixed position is located between the operation end and one of the plurality of rotatable joints adjacent to the operation end.

In an embodiment, the fixed position corresponds to a space-coordinate data and a joint-angle data. The numerical range of the joint-angle data is within a first set formed by angles of the plurality of rotatable joints. The numerical range of the space-coordinate is within a second set formed by the coordinates of the Cartesian coordinate system. The joint-angle data are converted to a space-coordinate data by non-linear transformation. When the sensor signal fulfills the default condition, the control unit provides a driving data to rotate the rotatable joints and move the robotic arm without interfering with the operator, and the driving data is within the scope of the first set, and the driving data is within the scope of null space of non-linear transformation.

In an embodiment, the operation end includes a fastening component that is used to hold an endoscope. When the operation end holds the endoscope and reaches an in vivo space through a skin incision, the fixed position is the point on the robotic arm near the skin incision.

In an embodiment, the sensor unit comprises a six-axis sensor disposed at a position adjacent to the operation end. The six-axis sensor provides at least one external force signal and at least one torque signal.

In an embodiment, the default condition is fulfilled when the external force signal and torque signal exceed a default threshold.

In an embodiment, a path used by the robotic arm to avoid the operator is produced based on the external force signal and the torque signal.

In an embodiment, a path of movement of the robotic arm is derived according to a small-mass dynamic model.

In an embodiment, the sensor unit includes an image capture component. The sensor signal includes a location information derived according to an image of the operator.

In an embodiment, the default condition is fulfilled when the distance between the operator and the robotic arm is less than a default threshold.

In an embodiment, the path used by the robotic arm to avoid the operator is determined by a path of movement of the operator after data extracted from the image of the operator fulfills the default condition.

From the above, the robotic arm of the present invention moves according to the force applied by the operator or the location of the operator. The operator controls the robotic arm by dragging-teaching or avoidance. Also, the robotic arm remains at a fixed position to provide well-functioning assistance in operations.

DETAILED DESCRIPTION

The robotic arm of the present invention is, for example, an automatic control device with a plurality of joints moving in a three-dimensional space. Preferably, the robotic arm of the present invention is, for example, a six-axis robotic arm with a plurality of rotatable joints which extend along two or more directions to different locations in a three-dimensional space. The following embodiments utilize a six-axis robotic arm as an examples; however, the present invention is not limited by the number of rotation axes of the robotic arm and the type of the robotic arm.

Figure 1:
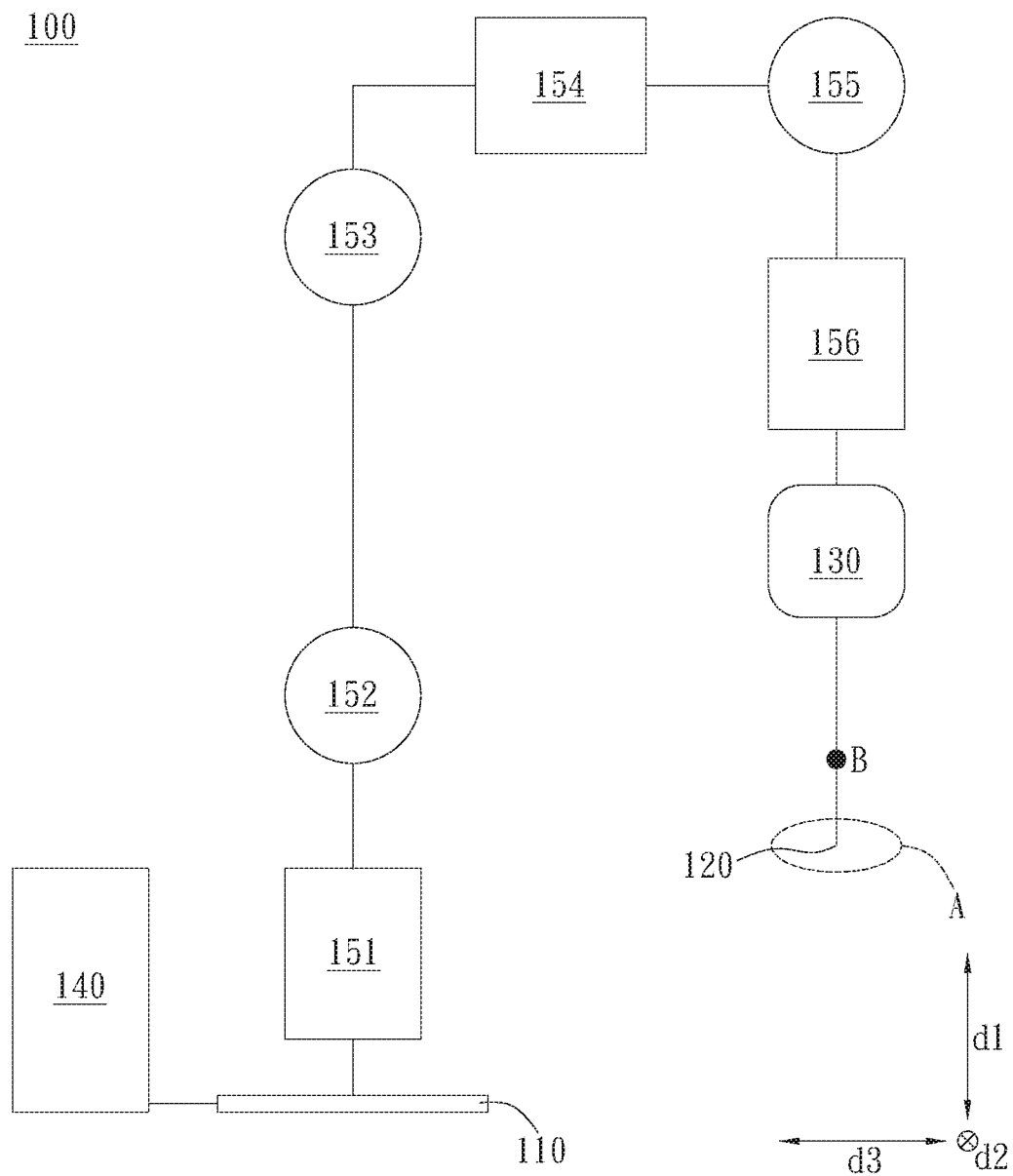
FIG. 1 is a schematic view of a robotic arm according to the first embodiment.

FIG. 1 is a schematic view of a robotic arm according to the first embodiment. Refer to FIG. 1. The robotic arm 100 includes, for example, a base 110 and operation end 120. The operation end 120 is connected to the base 110 and suitable for reaching an operational area A. The robotic arm 100 also includes a control unit 140 and plurality of joints 151-156. The control unit 140 is configured to control the joints disposed between the base 110 and the operation end 120 in the robotic arm 100 to adjust the location and angle of the operation end 120.

For instance, the robotic arm 100 is, for example, a six-axis robotic arm RA605 (Hiwin, TW). FIG. 1 is a schematic view exemplarily corresponding to each joint of the robotic arm 100. The control unit 140 is, for example, a robotic controller of compound type configured to control robotic arm 100. It should be stated that controlling the robotic arm 100 further includes but not limited to, for example, providing instruction signals, receiving feedback signals from drivers of joints 151-156, performing a floating-point calculation for the feedback signals and so on.

The robotic arm further comprises a sensor unit 130. In this embodiment, the sensor unit 130 is placed at an end adjacent to joint 156, that is, a location between the operation end 120 and joint 156. More specifically, the joints 151-156 of the robotic arm 100 rotate around different axes respectively. Take for example the robotic arm illustrated in FIG. 1. The joints 151, 153 and 155 may allow their two ends to rotate along an axis that is parallel to d1; the joints 152, 153 and 155 may allow their two ends to rotate along an axis that is parallel to d2, that is, a direction projected vertically to the graphic surface; the joint 154 may allow its two ends to rotate along an axis that is parallel to d3. Hence, after setting the base 110 as an origin in the space and rotating those joints 151-156, the part adjacent to joint 156 could have a relatively maximum degree of freedom to move or rotate in the three-dimensional space. Thus, the sensor unit 130 adjacent to joint 156 could easily measure the external force applied to the robotic arm.

Figure 2:
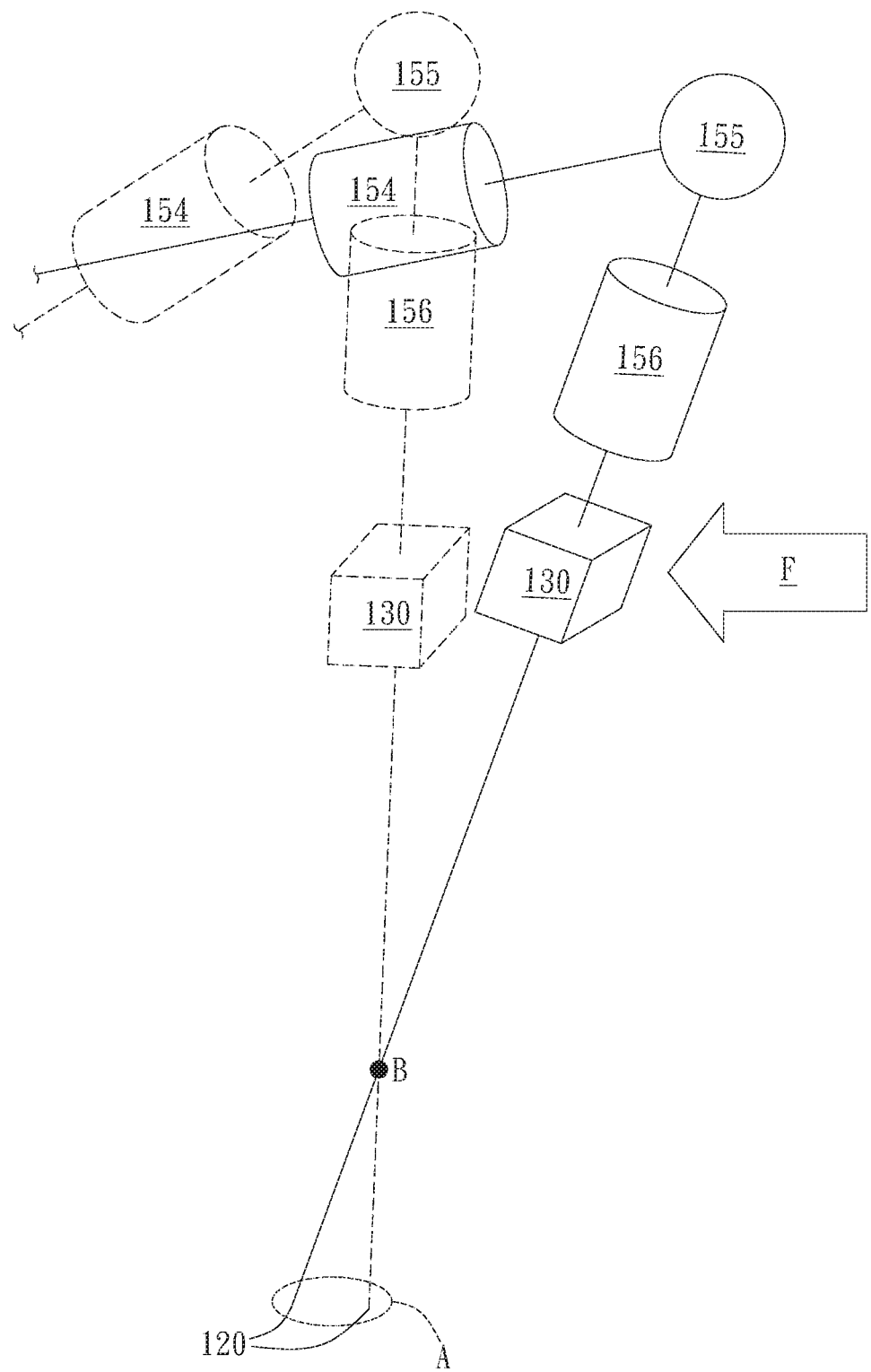
FIG. 2 is a schematic view of a part of the robotic arm according to the first embodiment when force is applied thereto.

FIG. 2 illustrates the schematic view of a part of the robotic arm 100 when an external force F is applied, wherein the schematic view of the pre-force condition is shown in solid lines; the post-force condition is shown in dash lines. Please note, the sensor unit 130 of this embodiment is disposed at the end of the robotic arm 100 to sense the force (F) applied to the end of the robotic arm by the operator. The control unit 140 converts the force measured by the sensor unit 130 to motion instructions to the robotic arm 100 which will cause the robotic arm to move correspondingly with the force F. At the same time, a fixed position B will be fixed during the motion of the robotic arm 100 so that when the robotic arm 100 is used in a procedure of medical surgery, the robotic arm will not only adjust its position by an external force, but will also fix the position where the operation end is inserted into the patient's body (i.e., the fixed position B). In brief, the robotic arm 100 could provide a safe way to operate, preferably, a way to operate by dragging-teaching. The robotic arm 100 provides good surgical assistance when it is used as an endoscope holder in a minimally invasive surgery.

More specifically, the robotic arm 100 of the present invention takes into account, for example, each condition that a doctor operating the robotic arm encounters, meets the need of the operator to move quickly to a desired location and position, and decreases stiffness or resistance of joints 151-156 to reduce stiffness of the robotic arm 100. At the same time, the sensor unit 130 senses the desired location and position of the operator and lets the operator drag and move the robotic arm 100.

The sensor unit 130 is disposed between the operation end 120 used for holding an endoscope and joint 156. Therefore, the sensor unit 130 or control unit 140 can perform a calibration according to the gravity applied to the endoscope, that is, the weight of the endoscope located at the operation end 120. The control unit 140 can further eliminate environmental interference and/or noise formed in the sensor signal caused by self-vibration of the robotic arm 100. Subsequently, the control unit 140 produces control signals for controlling joints 151-156 by means of, for example, a transfer matrix used to convert the sensor signal provided by sensor unit 130.

The signal transformation mentioned above is, for example, using a small-mass dynamic model to convert the signal provided by the sensor unit 130 to produce a path of movement for the robotic arm and based on the path of movement to provide the control signals to control joints 151-156. In detail, the small-mass dynamic model mentioned above is, for example, a model that minimizes the mass of the end of the robotic arm 100. When the sensor unit 130 monitors external forces, the control unit 140 calculates the direction of the resultant force and derives a desired path from an algorithm. The calculation is done by means of the movement behavior model of the small-mass dynamic model mentioned above.

The location of the operation end 120 and the fixed position B of the robotic arm 100 is determined by two sets of space data. One is the space-coordinate data and the other is the joint-angle data. The joint-angle data is within a set of rotation angle, more specifically, a set formed by the rotation angles of joints 151-156. The operation end 120 and fixed position B are determined by a plurality of angle value $q_i$. The space-coordinate data is within the set formed by Cartesian coordinates.

In detail, the location and position of the robotic arm 100 can be represented by, for example, Denavit Hartenberg parameters and the linkages between joints can be represented by a matrix of Homogeneous transformation as:

$$_0^6T = {_0^1T} \, {_1^2T} \, {_2^3T} \, {_3^4T} \, {_4^5T} \, {_5^6T}$$

wherein $_0^6T$ includes the location and the position of the end of the robotic arm 100, corresponding to three values of the Cartesian coordinate and three vectors that are orthogonal to each other, and can be simplified to:

$$x = f(q)$$

where x is the space-coordinate data mentioned above; q includes a plurality of joint-angle data $q_i$. The correlation mentioned above can be but not limited to, for example, non-linear transformation or space transformation to transform joint-angle data to space-coordinate data. When the space-coordinate data of the fixed position B is represented as x, the coordinate of the fixed position B is $x_{b,fix}$. When the robotic arm performs actions mentioned above, the coordinate of the fixed position B $x_{b,fix}$ will be within a null space of the transformation, that is to say, each q in the null space meets the formula below:

$$f(q) - x_{b,fix} = 0$$

Hence, the fixed position B will not change during the moving of the robotic arm 100.

In other words, when the robotic arm 100 is executing a motion mission computed based on the sensor signal of the sensor unit 130 and range of the motion mission is smaller than the degree of freedom of the robotic arm 100, the robotic arm is available to execute additional missions based on the remaining degree of freedom, for instance, changing the position of the operation end 120 while fixing itself at the fixed point B, and the additional mission is within in the null space mentioned above. At this time, the robotic arm 100 keeps itself at the fixed position B by rotating the joints 151-156, and at the same time changes the position of the robotic arm 100 to carry out instructions from the operator via the operator's dragging of the robotic arm 100.

Figure 3:
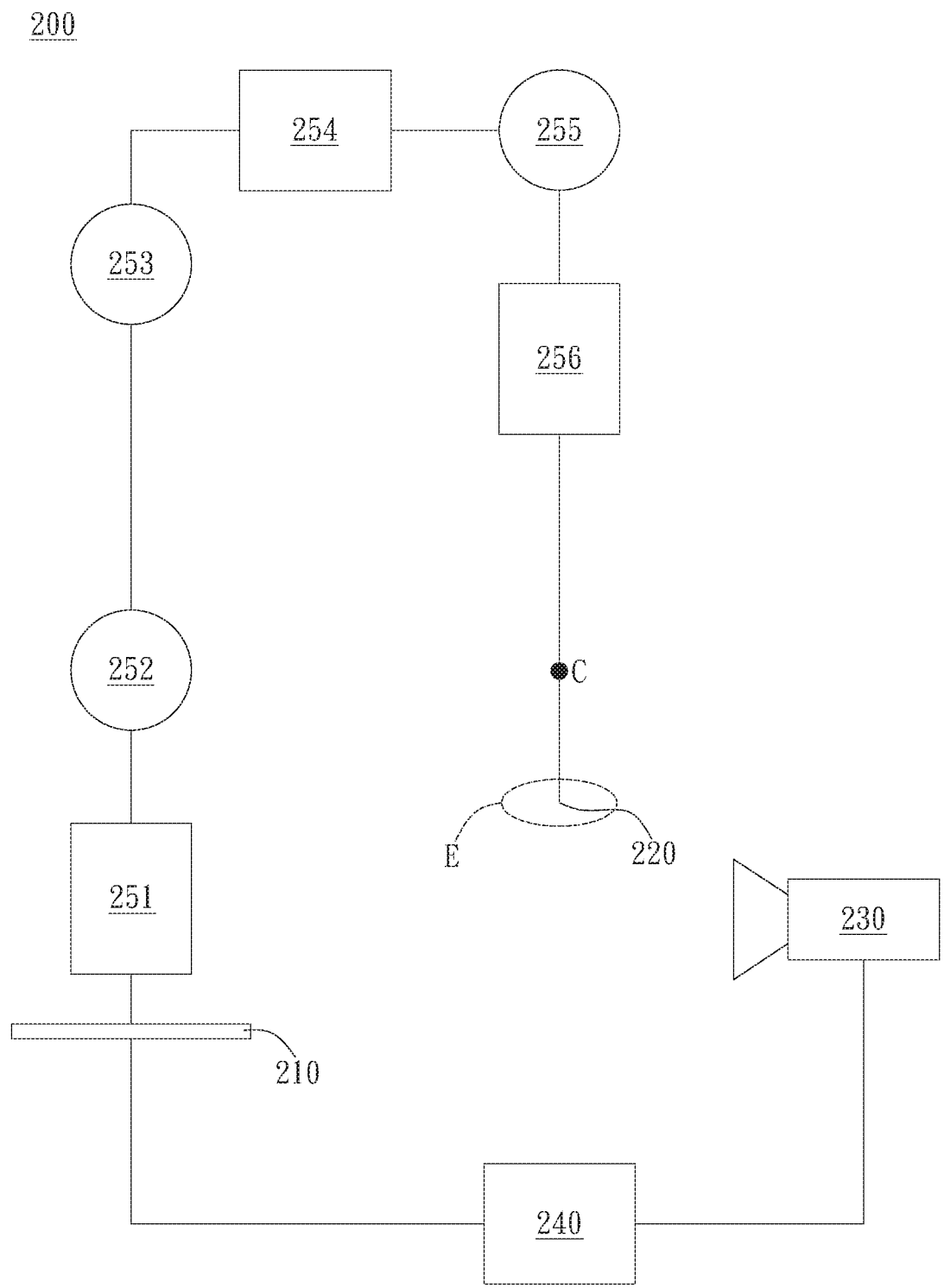
FIG. 3 is a schematic of a robotic arm according to the second embodiment.

However, a robotic arm of the present invention is not limited by the embodiment mentioned above which uses a six-axis sensor for sensor unit 130. FIG. 3 is a schematic view of a robotic arm according to the second embodiment. A robotic arm 200 comprises a base 210, joints 251-256, operation end 220 and control unit 240. The difference between the robotic arm 200 and the robotic arm 100 of the first embodiment mentioned above is that the sensor unit 230 of the robotic arm 200 is an image capture component configured to capture the image of the operator. Deriving a location information of the operator from the image computed by, for example, a processor of the sensor unit 230 or a processor of the control unit 240.

Figure 4:
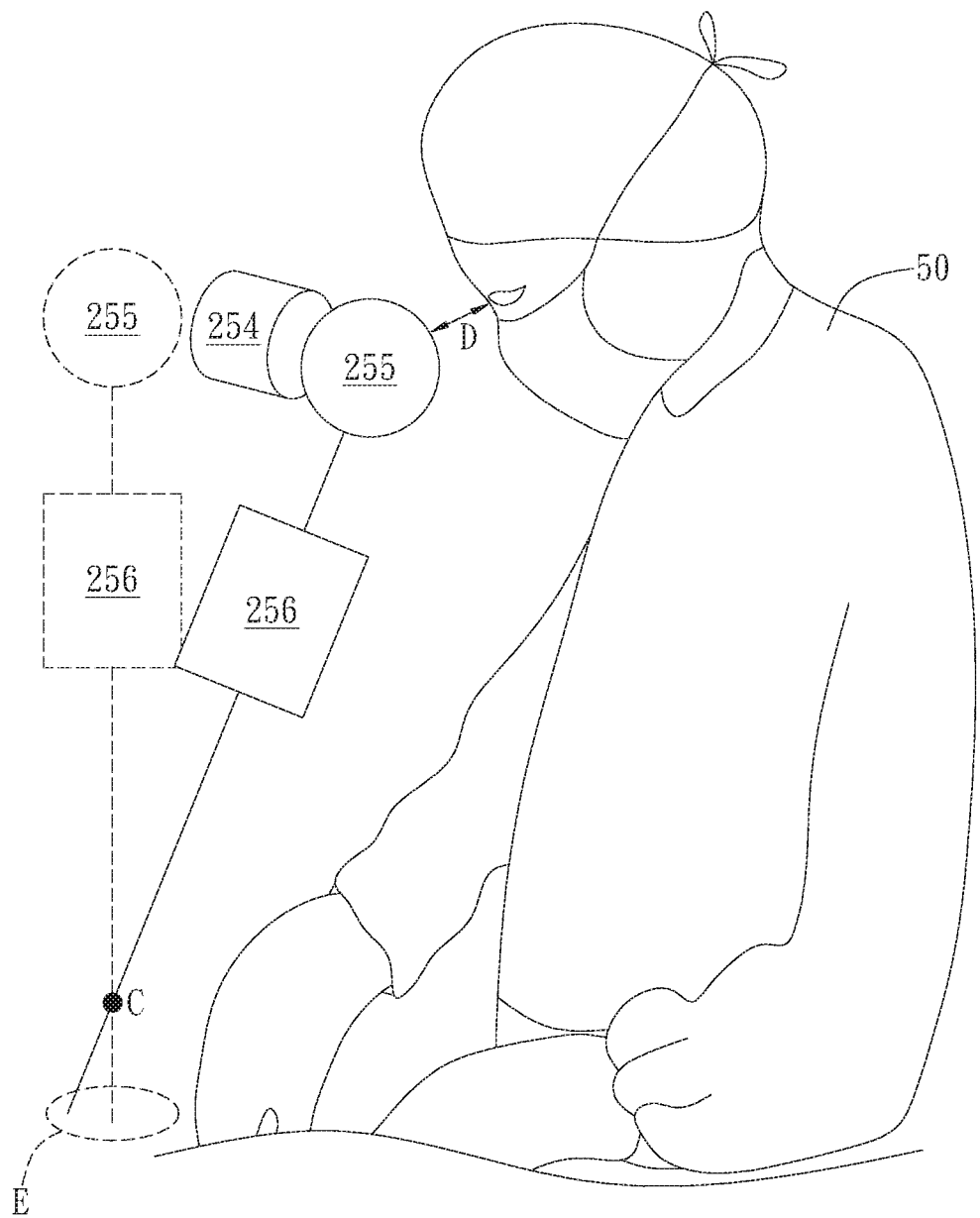
FIG. 4 is a schematic view of a part of the robotic arm according to the second embodiment when an image is detected thereby.

FIG. 4 is a schematic view of image capturing by the sensor unit 230. Refer to FIG. 4. It illustrates a partial robotic arm 200 and an operator 50. The sensor unit 230 derives the body frame of the operator 50 via an image and measures the distance D between the body frame of the operation 50 and the robotic arm 200. The robotic arm 200 sets a default threshold. The default condition where the robotic arm 200 moves and avoids the operator 50 is when the distance D is less than the threshold. When the distance D is less than the threshold, the robotic arm 200 will avoid the operator 50 and keep itself at a fixed position C which is between an operational area E and the joint 256.

To derive the distance between the body frame of the operator 50 and the robotic arm 200, for example, one can compute the distance between one of the joints 251-256 and the location of the body frame of the operator 50, or use all joints 251-256 or the location of the linkages between each joint and the location of the body frame of the operator 50 to compute the distance, and execute the avoid instructions when one of those distances is less than the default threshold. In short, this embodiment provides an operation method to control the robotic arm 200 through avoidance, which is based on an image captured by the sensor unit 230 to avoid obstacles around the robotic arm 200.

The motion of robotic arm 200 is similar to that of the robotic arm 100 mentioned above. Based on the transformation of null space, the robotic arm 200 can remain at the fixed position C while moving.

Based on the foregoing, the robotic arm of the present invention could move according to an applied force and the location of an operator, and remain at a fixed position after arriving at an operational area. Hence, an operator could operate the robotic arm through dragging or avoidance. At the same time, the robotic arm could move in the way that a part of it is fixed at a certain position to provide a safer, more intuitive, and more convenient way to assist in operations.

The invention claimed is:

1. A robotic arm for assisting an operator, comprising:
   an operation end;
   a base connected to the operation end;
   a sensor unit configured to provide a sensor signal based on a movement of the operator or a force applied by the operator; and
   a control unit configured to control a motion of the robotic arm and to move the operation end, wherein when the operation end reaches an operational area, the control unit sets a fixed position on the robotic arm between the base and the operation end;
   wherein when a distance, according to the sensor signal, between the operator and the robotic arm is less than a default threshold, the sensor signal fulfills a default condition, the robotic arm moves without interfering with the operator, and the fixed position remains immovably during the movement of the robotic arm;
   wherein a moving path of the robotic arm is derived by converting the sensor signal according to a small-mass dynamic model;
   wherein the small-mass dynamic model is a model that minimizes the mass of the operation end of the robotic arm.

2. The robotic arm of claim 1, further comprising:
   a plurality of rotatable joints connected between the operation end and the base, wherein the fixed position is located between the operation end and one of the plurality of rotatable joints adjacent to the operation end.

3. The robotic arm of claim 2, wherein the fixed position corresponds to a space-coordinate data and a joint-angle data, a numerical range of the joint-angle data is within a first set of angles of the plurality of rotatable joints, a numerical range of the space-coordinate is within a second set of coordinates of Cartesian coordinate system, the joint-angle data are converted to the space-coordinate data by a transformation;
   when the sensor signal fulfills the default condition, the control unit provides a driving data to rotate the rotatable joints and moves the robotic arm without interfering with the operator, and the driving data is within the scope of the first set of coordinates, and the driving data is within a scope of null space of the transformation.

4. The robotic arm of claim 1, wherein the operation end includes:
   a fastening component for holding an endoscope;
   when the operation end holds the endoscope and reaches an in vivo space through a skin incision, the fixed position is on the robotic arm and near the skin incision.

5. The robotic arm of claim 1, wherein the sensor unit includes:
   a six-axis sensor configured adjacent to the operation end, wherein the six-axis sensor provides at least one external force signal and at least one torque signal.

6. The robotic arm of claim 5, wherein the default condition is further fulfilled when the external force signal and torque signal exceed a default threshold.

7. The robotic of the claim 5, wherein a path of the robotic arm avoiding the operator is produced in view of the external force signal and the torque signal.

8. The robotic of claim 1, wherein the sensor unit includes:
   an image capture component, the sensor signal comprises a location information derived from an image of the operator.

9. The robotic arm of claim 8, wherein a path of the robotic arm avoiding the operator is determined by a moving path of the operator after data extracted from the image of the operator fulfill the default condition.

* * * * *